United States Patent

Inukai et al.

[11] Patent Number: 6,036,652
[45] Date of Patent: Mar. 14, 2000

[54] BLOOD PRESSURE ESTIMATING APPARATUS AND METHOD

[75] Inventors: Hidekatsu Inukai, Nagoya; Akihiro Yokozeki; Keizoh Kawaguchi, both of Komaki; Kiyoyuki Narimatsu, Kasugai, all of Japan

[73] Assignee: Colin Corporation, Komaki, Japan

[21] Appl. No.: 09/086,749

[22] Filed: May 29, 1998

[30] Foreign Application Priority Data

May 12, 1998 [JP] Japan .................................. 10-128491

[51] Int. Cl.⁷ ....................................................... A61B 5/02
[52] U.S. Cl. ........................... 600/493; 600/494; 600/485; 600/490
[58] Field of Search ..................................... 600/493, 490, 600/491, 492, 494, 495, 499

[56] References Cited

U.S. PATENT DOCUMENTS

| | | | |
|---|---|---|---|
| 5,131,391 | 7/1992 | Sakai et al. ............................... | 600/310 |
| 5,653,241 | 8/1997 | Harada et al. ............................ | 600/490 |
| 5,743,857 | 4/1998 | Shinoda et al. .......................... | 600/496 |
| 5,776,071 | 7/1998 | Inukai et al. ............................. | 600/493 |
| 5,830,148 | 11/1998 | Inukai et al. ............................. | 600/481 |
| 5,830,149 | 11/1998 | Oka et al. ................................ | 600/500 |
| 5,853,371 | 12/1998 | Inukai et al. ............................. | 600/483 |
| 5,865,756 | 2/1999 | Peel, III .................................. | 600/490 |

FOREIGN PATENT DOCUMENTS 7-9305 U   2/1995   Japan .
7-308295   11/1995  Japan .

*Primary Examiner*—Cary O'Connor
*Assistant Examiner*—Navin Natnithithadha
*Attorney, Agent, or Firm*—Oliff & Berridge, PLC

[57] ABSTRACT

An apparatus for successively estimating an intraarterial blood pressure of a living subject, based on information non-invasively obtained from a circulatory organ of the subject, including: a first device for non-invasively obtaining, from the circulatory organ of the subject, first information which relates to velocity of propagation of a pulse wave which propagates through an artery of the subject; a second device for non-invasively obtaining, from the circulatory organ of the subject, at least one of second information which relates to heart rate of the subject and third information which relates to an area defined by a volume pulse wave from a peripheral portion of the subject; and a third device for estimating, according to a predetermined relationship between (A) blood pressure, and (B1) first information and (B2) at least one of (B21) second information and (B22) third information, the intraarterial blood pressure of the subject, based on the first information obtained by the first device and the at least one of the second information and the third information obtained by the second device.

14 Claims, 10 Drawing Sheets

FIG. 5

| BLOOD-PRESSURE RANGES (mmHg) COEFFICIENTS | ~40 | ~80 | ~120 | ~160 | ~200 | 200~ |
|---|---|---|---|---|---|---|
| α | α1 | α2 | α3 | α4 | α5 | α6 |
| β | β1 | β2 | β3 | β4 | β5 | β6 |
| γ | γ1 | γ2 | γ3 | γ4 | γ5 | γ6 |

$(\alpha > 0, \beta, \gamma < 0)$

BLOOD PRESSURE ESTIMATING APPARATUS AND METHOD

BACKGROUND OF THE INVENTION

1. Field of the Invention

The present invention relates to a blood pressure estimating apparatus and method for successively estimating an intraarterial blood pressure of a living subject, based on information non-invasively obtained from a circulatory organ of the subject.

2. Related Art Statement

There is known, as a blood pressure measuring apparatus for non-invasively measuring an intraarterial blood pressure of a subject, a so-called Korotokoff-sound blood pressure measuring apparatus or oscillometric blood pressure measuring apparatus. The Korotokoff-sound blood pressure measuring apparatus determines a blood pressure of the subject, based on a pressing pressure of a pressing band being wound around a portion of the subject at the time of occurrence or disappearance of Korotokoff sounds produced by changing the pressing pressure of the pressing band. The oscillometric blood pressure measuring apparatus determines a blood pressure of the subject, based on variation of amplitude of a pulse wave produced while the pressing pressure of the pressing band is changed.

In an operating room, an intensive care unit, or the like, it is needed to successively measure a blood pressure of a subject when an urgent medical treatment or cure is required. In the case where the above conventional blood pressure measuring apparatus is used, it takes several tens of seconds from a start of the blood pressure measurement to obtain a blood pressure of the subject. Moreover, if an interval between successive blood pressure measurements is shortened to obtain a blood pressure at a relatively short period, congestion occurs to a body portion of the subject due to high frequency of pressing of the pressing band, whereby errors occur to the blood pressure measurements.

Further, there has been proposed a blood pressure estimating apparatus including means for calculating a velocity of propagation of a pulse wave which propagates through an artery of the subject, and means for successively estimating, according to a predetermined relationship between blood pressure and velocity of propagation of pulse wave, an intraarterial blood pressure of the subject, based on the calculated velocity of propagation of the pulse wave. An example of the blood pressure estimating apparatus is disclosed in Laid-open Publication No. 7-9305 of unexamined Japanese Utility Model Application and Laid-open Publication No. 7-308295 of unexamined Japanese Patent Application.

Thus, the above blood pressure estimating apparatus discloses only a technique to successively estimate the blood pressure based on a propagation time of a pulse wave or a propagation velocity of a pulse wave. In the case where the blood pressure is estimated based on only the pulse-wave propagation time or the pulse-wave propagation velocity, the blood pressure can not enjoy high accuracy. Therefore, it is needed to frequently calibrate the estimating apparatus, based on an actual blood pressure measured by the Korotokoff-sound blood pressure measuring apparatus or the oscillometric blood pressure measuring apparatus.

SUMMARY OF THE INVENTION

It is therefore a first object of the present invention to provide a blood pressure estimating apparatus which estimates, with high accuracy, a blood pressure of a living subject.

It is a second object of the present invention to provide a method of estimating a blood pressure of a living subject with high accuracy.

The first object has been achieved by the present invention. According to a first aspect of the present invention, there is provided an apparatus for successively estimating an intraarterial blood pressure of a living subject, based on information non-invasively obtained from a circulatory organ of the subject, comprising: (a) first means for non-invasively obtaining, from the circulatory organ of the subject, first information which relates to velocity of propagation of a pulse wave which propagates through an artery of the subject; (b) second means for non-invasively obtaining, from the circulatory organ of the subject, at least one of second information which relates to heart rate of the subject and third information which relates to an area defined by a volume pulse wave from a peripheral portion of the subject; and (c) third means for estimating, according to a predetermined relationship between (A) blood pressure, and (B1) first information and (B2) at least one of (B21) second information and (B22) third information, the intraarterial blood pressure of the subject, based on the first information obtained by the first means and the at least one of the second information and the third information obtained by the second means.

In the estimating apparatus in accordance with the first aspect of the invention, the third means estimates, according to a predetermined relationship between (A) blood pressure, and (B1) first information and (B2) at least one of (B21) second information and (B22) third information, an intraarterial blood pressure of the subject, based on the first information obtained by the first means and the at least one of the second information and the third information obtained by the second means. For example, as compared with the case where a blood pressure is estimated based on only the first information, the present apparatus estimates the intraarterial blood pressure, based on, in addition to the first information, at least one of the second information as a parameter on the side of the heart of the subject which changes in relation with the blood pressure and the third information as a parameter on the side of a peripheral portion of the subject which changes in relation with the blood pressure. Accordingly, the accuracy of the estimated blood pressure is improved.

According to a preferred feature of the first aspect of the invention, the second means comprises means for obtaining the second information and the third information, and the third means comprises means for estimating, according to the predetermined relationship between (A) blood pressure, and (B1) first information, (B21) second information, and (B22) third information, the intraarterial blood pressure of the subject, based on the obtained first information, the obtained second information, and the obtained third information. In the above apparatus, the third means estimates the intraarterial blood pressure based on the second information as the parameter on the side of the heart of the subject and the third information as the parameter on the side of the peripheral portion of the subject as well as the first information. In this case, it is not needed to frequently calibrate the estimating apparatus, based on an actual blood pressure of the subject measured by using a pressing band, because the estimated blood pressure enjoys higher accuracy in comparison with an estimated blood pressure which is estimated based on only the first information.

According to another feature of the first aspect of the invention, the first means comprises means for obtaining, as the first information, a time, DT, needed for the pulse wave to propagate between two different portions of the artery, the second means comprises means for obtaining, as the second information, a heart-beat period, RR, of the subject, and means for obtaining, as the third information, a ratio, VR, of the area of the volume pulse wave to the heart-beat period RR, and the third means comprises means for estimating, according to the predetermined relationship between (A) blood pressure, EBP, and (B1) time DT, (B21) period RR, and (B22) ratio VR, defined by a following expression: $EBP=\alpha(1/DT)+\beta RR+\gamma VR+\delta$, where $\alpha$, $\beta$, and $\gamma$ are predetermined coefficients and $\delta$ is a predetermined constant, the intraarterial blood pressure of the subject, based on the obtained time DT, the obtained period RR, and the obtained ratio VR. The two different portions of the artery may comprise the heart and capillaries of the subject. In the above apparatus, the third means estimates the intraarterial blood pressure based on the second information as the parameter on the side of the heart of the subject and the third information as the parameter on the side of the peripheral portion of the subject as well as the first information. In this case, it is not needed to frequently calibrate the present apparatus, based on an actual blood pressure of the subject measured by using a pressing band, because the estimated blood pressure enjoys higher accuracy in comparison with an estimated blood pressure which is estimated based on only the first information.

According to another feature of the first aspect of the invention, the apparatus further comprising a memory which stores data indicative of the coefficients $\alpha$, $\beta$, $\gamma$ which are predetermined by applying a multiple regression analysis to a plurality of sets of information obtained from at least one living person, each of the sets of information comprising a blood pressure obtained from the person, and a time DT, a period RR, and a ratio VR obtained from the person when the blood pressure is obtained from the person. Accordingly, the present apparatus can obtain a useful relationship for calculating an estimated blood pressure.

According to another feature of the first aspect of the invention, the second means comprises means for obtaining the third information selected from the group consisting of the area defined by the volume pulse wave, a ratio of the area to a heart-beat period of the subject, a ratio of the area to a product of the heart-beat period and an amplitude of the volume pulse wave, and a ratio of a product of the area and the amplitude to the heart-beat period.

According to another feature of the first aspect of the invention, the first means comprises: a first pulse-wave sensor and a second pulse-wave sensor which non-invasively detect the pulse wave from two different portions of the artery of the subject, respectively; and means for determining, as the first information, a time needed for the pulse wave to propagate between the two different portions.

According to another feature of the first aspect of the invention, the second means comprises means for determining, as the second information, a time difference between respective predetermined points of successive two heartbeat-synchronous pulses of the pulse wave detected by one of the first and second pulse-wave sensors.

According to another feature of the first aspect of the invention, the second means comprises one of the first and second pulse-wave sensors, the one pulse-wave sensor detecting the volume pulse wave from the peripheral portion of the subject.

According to another feature of the first aspect of the invention, the first and second pulse-wave sensors comprise an electrocardiograph and a photoelectric oximeter.

The second object has been achieved by the present invention. According to a second aspect of the present invention, there is provided a method of successively estimating an intraarterial blood pressure of a living subject, based on information non-invasively obtained from a circulatory organ of the subject, comprising the steps of: (a) non-invasively obtaining, from the circulatory organ of the subject, first information which relates to velocity of propagation of a pulse wave which propagates through an artery of the subject, (b) non-invasively obtaining, from the circulatory organ of the subject, at least one of second information which relates to heart rate of the subject and third information which relates to an area defined by a volume pulse wave from a peripheral portion of the subject, and (c) estimating, according to a predetermined relationship between (A) blood pressure, and (B1) first information and (B2) at least one of (B21) second information and (B22) third information, the intraarterial blood pressure of the subject, based on the obtained first information and the obtained at least one of the second information and the third information.

In the method in accordance with the second aspect of the present invention, an intraarterial blood pressure of the subject is estimated, according to a predetermined relationship between (A) blood pressure, and (B1) first information and (B2) at least one of (B21) second information and (B22) third information, based on the obtained first information and the obtained at least one of the second information and the third information. For example, as compared with the case where a blood pressure is estimated based on only the first information, the present method estimates the intraarterial blood pressure, based on, in addition to the first information, at least one of the second information as a parameter on the side of the heart of the subject which changes in relation with the blood pressure and the third information as a parameter on the side of a peripheral portion of the subject which changes in relation with the blood pressure. Accordingly, the accuracy of the estimated blood pressure is improved.

According to a preferred feature of the second aspect of the invention, the step of obtaining the at least one of the second information and the third information comprises obtaining the second information and the third information, and the step of estimating the intraarterial blood pressure of the subject comprises estimating, according to the predetermined relationship between (A) blood pressure, and (B1) first information, (B21) second information, and (B22) third information, the intraarterial blood pressure of the subject, based on the obtained first information, the obtained second information, and the obtained third information.

According to another feature of the second aspect of the invention, the step of obtaining the first information comprises obtaining a time, DT, needed for the pulse wave to propagate between two different portions of the artery, the step of obtaining the at least one of the second information and the third information comprises obtaining, as the second information, a heart-beat period, RR, of the subject and obtaining, as the third information, a ratio, VR, of the area of the volume pulse wave to the heart-beat period RR, and the step of estimating the intraarterial blood pressure of the subject comprises estimating, according to the predetermined relationship between (A) blood pressure EBP, and (B1) time DT, (B21) period RR, and (B22) ratio VR, defined by a following expression: $EBP=\alpha(1/DT)+\beta RR+\gamma VR+\delta$, where $\alpha$, $\beta$, $\gamma$ are predetermined coefficients and $\delta$ is a predetermined constant, the intraarterial blood pressure of the subject, based on the obtained time DT, the obtained period RR, and the obtained ratio VR.

According to another feature of the second aspect of the invention, the method further comprises a step of determining the coefficients α, β, γ by applying a multiple regression analysis to a plurality of sets of information obtained from at least one living person, each of the sets of information comprising a blood pressure obtained from the person, and a time DT, a period RR, and a ratio RR obtained from the person when the blood pressure is obtained from the person.

According to another feature of the second aspect of the invention, the step of obtaining the at least one of the second information and the third information comprises obtaining the third information selected from the group consisting of the area defined by the volume pulse wave, a ratio of the area to a heart-beat period of the subject, a ratio of the area to a product of the heart-beat period and an amplitude of the volume pulse wave, and a ratio of a product of the area and the amplitude to the heart-beat period.

BRIEF DESCRIPTION OF THE DRAWINGS

The above and optional objects, features, and advantages of the present invention will better be understood by reading the following detailed description of the preferred embodiments of the invention when considered in conjunction with the accompanying drawings, in which:

FIG. 5 is a view to show a plurality of groups of predetermined coefficients for an expression (2) which correspond to a plurality of blood-pressure ranges, respectively;

DETAILED DESCRIPTION OF THE PREFERRED EMBODIMENT

Figure 1:
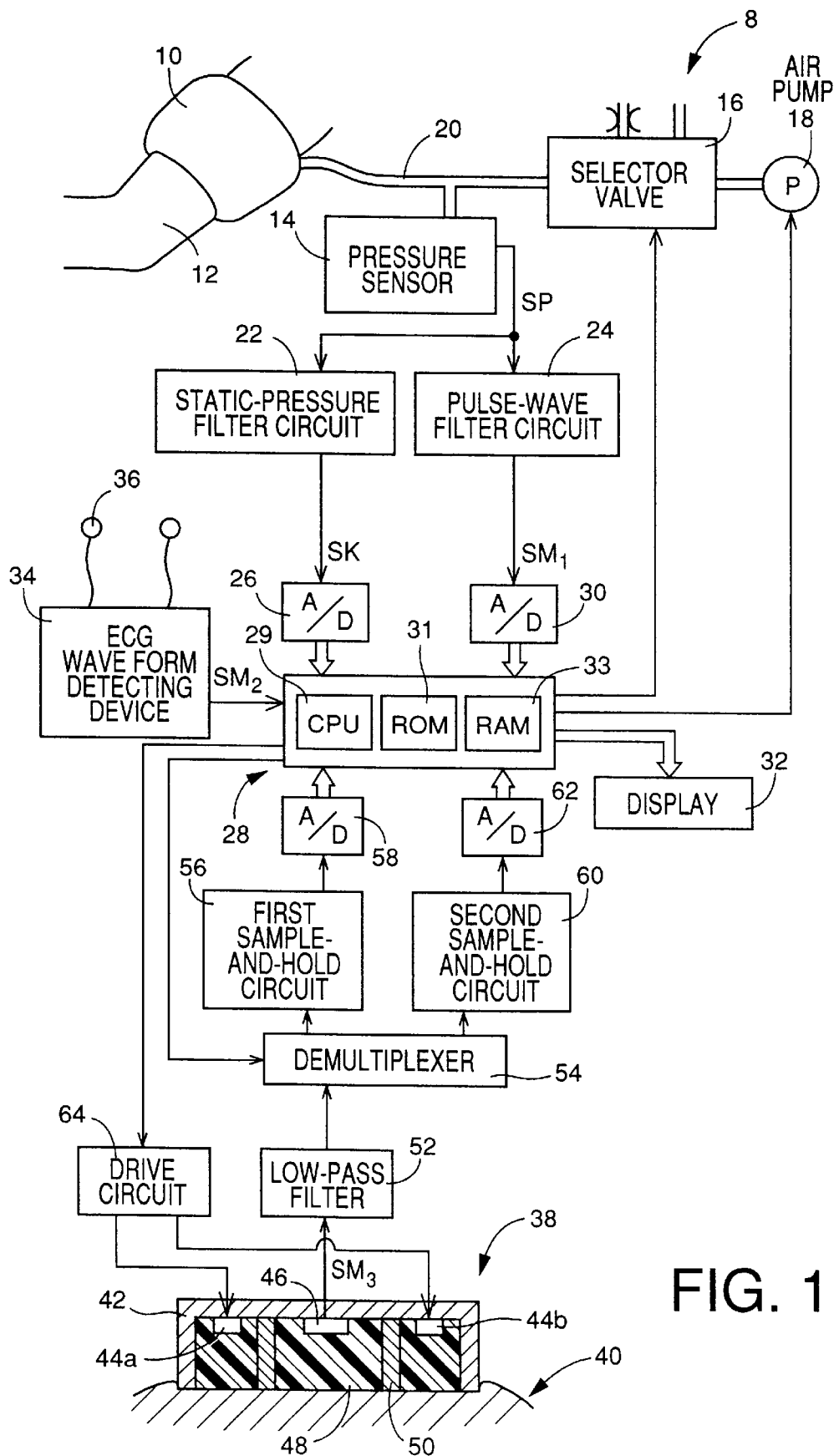
FIG. 1 is a diagrammatic view of a blood pressure estimating apparatus 8 embodying the present invention.

Referring to FIG. 1, there will be described a blood pressure (BP) estimating apparatus 8 embodying the present invention.

In FIG. 1, the BP estimating apparatus 8 includes a cuff 10 which has a belt-like cloth bag and a rubber bag accommodated in the cloth bag and which is adapted to be wound around an upper arm 12 of a patient, for example, a pressure sensor 14, a selector valve 16 and an air pump 18 each of which is connected to the cuff 10 via a piping 20. The selector valve 16 is selectively placed in an inflation position in which the selector valve 16 permits a pressurized air to be supplied to the cuff 10, a slow-deflation position in which the selector valve 16 permits the pressurized air to be slowly discharged from the cuff 10, and a quick-deflation position in which the selector valve 16 permits the pressurized air to be quickly discharged from the cuff 10.

The pressure sensor 14 detects an air pressure in the cuff 10, and supplies a pressure signal SP representative of the detected pressure to each of a static pressure filter circuit 22 and a pulse-wave filter circuit 24. The static pressure filter circuit 22 includes a low-pass filter and extracts, from the pressure signal SP, a static component contained in the signal SP, i.e., cuff pressure signal SK representative of the static cuff pressure. The cuff pressure signal SK is supplied to an electronic control device 28 via an analog-to-digital (A/D) converter 26. The pulse-wave filter circuit 24 includes a band-pass filter and extracts, from the pressure signal SP, an oscillating component having predetermined frequencies, i.e., pulse-wave signal $SM_1$. The pulse-wave signal $SM_1$ is supplied to the electronic control device 28 via an A/D converter 30. The pulse-wave signal $SM_1$ represents an oscillatory pressure wave which is produced from a brachial artery (not shown) of the patient in synchronism with the heartbeat of the patient and is propagated to the cuff 10.

The electronic control device 28 is provided by a so-called microcomputer including a central processing unit (CPU) 29, a read only memory (ROM) 31, a random access memory (RAM) 33 and an input-and-output (I/O) port (not shown). The CPU 29 processes signals according to control programs pre-stored in the ROM 31 by utilizing a temporary-storage function of the RAM 33, and supplies drive signals to the selector valve 16 and the air pump 18 through the I/O port.

The BP estimating apparatus 8 further includes an electrocardiographic (ECG) waveform detecting device 34 which continuously detects an ECG waveform representative of an action potential of a cardiac muscle of a living subject, through a plurality of electrodes 36 being put on predetermined portions of the subject, and supplies an ECG waveform signal $SM_2$ representative of the detected ECG waveform to the electronic control device 28. The ECG waveform detecting device 34 is used for detecting a Q-wave or a R-wave of the ECG waveform which corresponds to a time point when the output of blood from the heart of the subject toward the aorta of the subject is started.

The BP estimating apparatus 8 still further includes a photoelectric pulse wave detecting probe 38 (hereinafter, referred to as the "probe") which is employed as part of a pulse oximeter. The probe 38 functions as a peripheral pulse wave detecting device for detecting a pulse wave propagated to a peripheral artery including capillaries. The probe 38 is adapted to be set on a skin or a body surface 40 of the subject, e.g., an end portion of a finger of the patient, with the help of a band (not shown) such that the probe 38 closely contacts the body surface 40. The probe 38 includes a container-like housing 42 which opens in a certain direction, a first and a second group of light emitting elements 44a, 44b, such as LEDs (light emitting diodes), which are disposed on an outer peripheral portion of an inner bottom surface of the housing 42 (hereinafter, referred to as the light emitting elements 44 in the case where the first and second group of light emitting elements 44a, 44b need not be discriminated from each other), a light receiving element 46, such as a photodiode or a phototransister, which is disposed on a central portion of the inner bottom surface of the housing 42, a transparent resin 48 which is integrally disposed in the housing 42 to cover the light emitting elements 44 and the light receiving element 46, and an annular shade member 50 which is disposed between the light emitting elements 44 and the light receiving element 46, for preventing the lights emitted toward the body surface 40 by the light emitting elements 44 and reflected from the body surface 40, from being received by the light receiving element 46.

The first and second groups of light emitting elements 44a, 44b emit a red light having about 660 nm wavelength and an infrared light having about 800 nm wavelength, respectively. The first and second light emitting elements 44a, 44b alternately emit the red and infrared lights at a predetermined frequency. The lights emitted toward the body surface 40 by the light emitting elements 44 are reflected from a body tissue of the subject where a dense capillaries occur, and the reflected lights are received by the common light receiving element 46. In place of the 660 nm and 800 nm wavelengths lights, the first and second light emitting elements 44a, 44b may employ various pairs of lights each pair of which have different wavelengths, so long as one light of each pair exhibits significantly different absorption factors with respect to oxygenated hemoglobin and reduced hemoglobin, respectively, and the other light exhibits substantially same absorption factors with respect to the two sorts of hemoglobin, i.e., has a wavelength which is reflected by each of the two sorts of hemoglobin.

The light receiving element 46 outputs, through a low-pass filter 52, a photoelectric pulse-wave signal $SM_3$ representative of an amount of the received light. The light receiving element 46 is connected to the low-pass filter 52 via an amplifier or the like. The low-pass filter 52 eliminates, from the photoelectric pulse-wave signal $SM_3$ input thereto, noise having frequencies higher than that of a pulse wave, and outputs the noise-free signal $SM_3$, to a demultiplexer 54. The photoelectric pulse wave represented by the photoelectric pulse-wave signal $SM_3$ can be said as a volume pulse wave produced in synchronism with a pulse of the patient. That is, the photoelectric pulse wave is a pulse-synchronous wave.

The demultiplexer 54 is alternately switched according to signals supplied thereto from the electronic control device 28 in synchronism with the light emissions of the first and second light emitting elements 44a, 44b. Thus, the demultiplexer 54 successively supplies, to the I/O port (not shown) of the electronic control device 28, an electric signal $SM_R$ representative of the red light through a first sample-and-hold circuit 56 and an A/D converter 58, and an electric signal $SM_{IR}$ representative of the infrared light through a second sample-and-hold circuit 60 and an A/D converter 62. The first and second sample-and-hold circuits 56, 60 hold the electric signals $SM_R$, $SM_{IR}$ input thereto, respectively, and do not output those electric signals to the A/D converters 58, 62, before the prior signals $SM_R$, $SM_{IR}$ are completely converted by the two A/D converters 58, 62, respectively.

In the electronic control device 28, the CPU 29 carries out a measuring operation according to control programs pre-stored in the ROM 31 by utilizing a temporary-storage function of the RAM 33. More specifically, the CPU 29 generates a light emit signal SLV to a drive circuit 64 so that the first and second light emitting elements 44a, 44b alternately emit the red and infrared lights at a predetermined frequency, respectively, such that each light emission lasts for a predetermined period. In synchronism with the alternate light emissions by the first and second light emitting elements 44a, 44b, the CPU 29 generates a switch signal SC to the demultiplexer 54 so as to correspondingly place the demultiplexer 54 in a first or a second position. Thus, the signals $SM_R$, $SM_{IR}$ are separated from each other by the demultiplexer 54 such that the signal $SM_R$ is supplied to the first sample-and-hold circuit 56 while the signal $SM_{IR}$ is supplied to the second sample-and-hold circuit 60. Further, the CPU 29 determines an oxygen saturation in the blood of the subject, based on respective amplitudes of the signals $SM_R$, $SM_{IR}$, according to a predetermined expression pre-stored in the ROM 31. The blood oxygen saturation determining method is disclosed in U.S. Pat. No. 5,131,391.

The BP estimating apparatus 8 further includes a display 32 which is connected to the electronic control device 28. The CPU 29 of the control device 28 supplies electric signals to the display 32. The display 32 includes a CRT (cathode ray tube) and a speaker.

Figure 2:
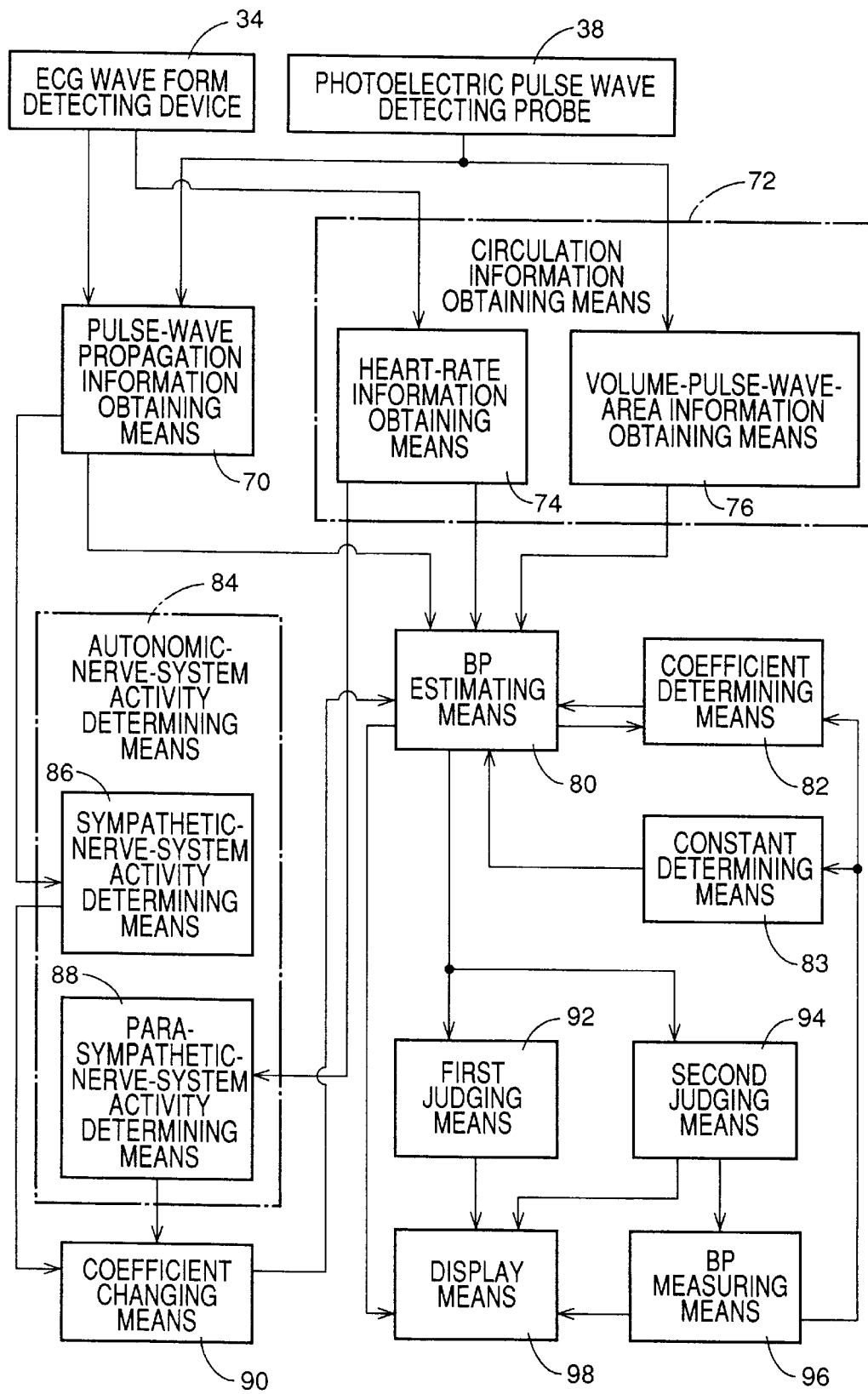
FIG. 2 is a block diagram for illustrating essential functions of an electronic control device 28 of the apparatus of FIG. 1.
Figure 3:
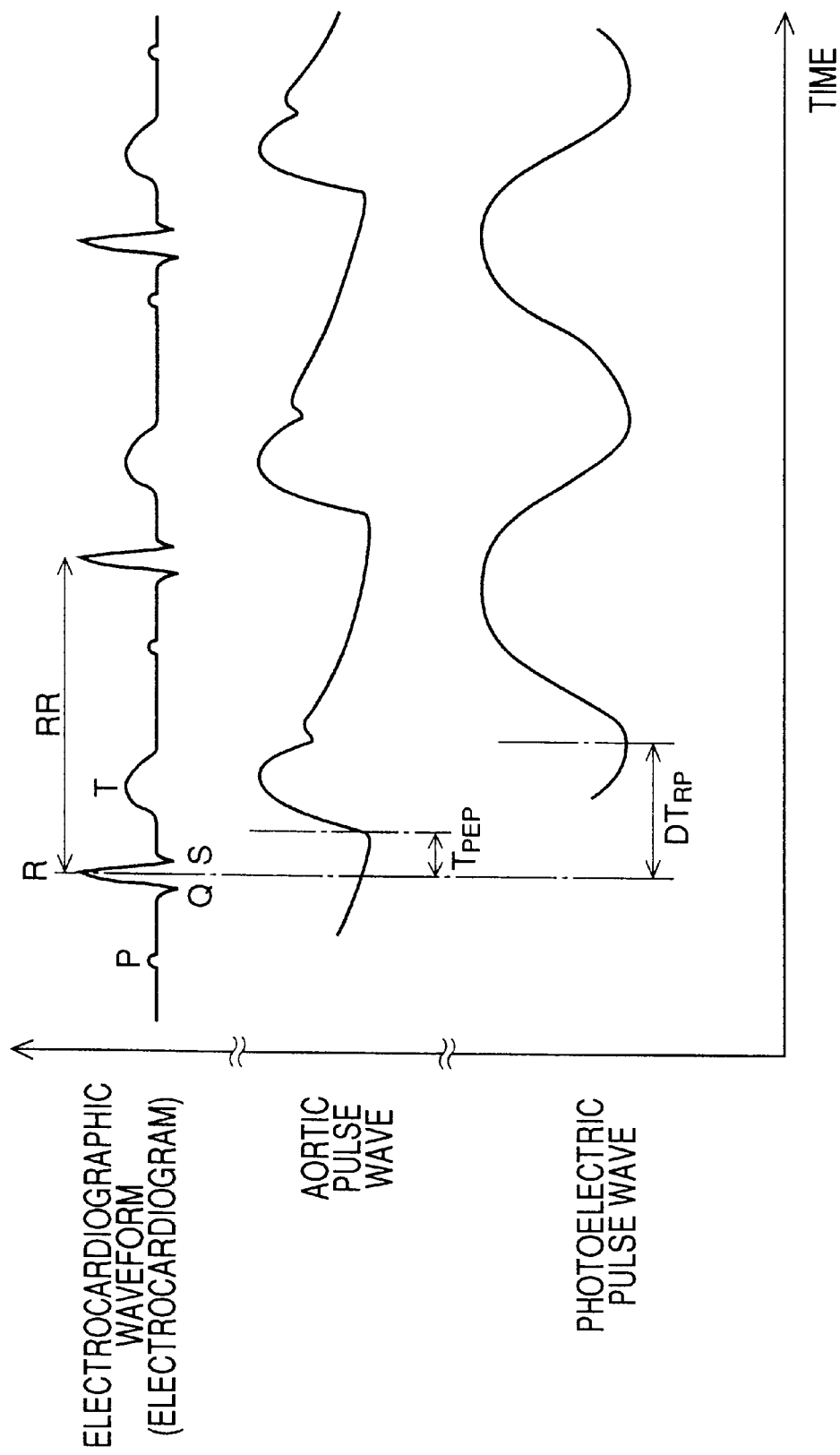
FIG. 3 is a view to show a time difference $DT_{RP}$ obtained by the operation of the electronic control device 28.

FIG. 2 illustrates essential functions of the electronic control device 28 of the present BP estimating apparatus 8. In the figure, a pulse-wave propagation (PWP) information obtaining means 70 obtains information which relates to a velocity $V_M$ of propagation of a pulse wave which propagates through an artery, such as a time $DT_{RP}$ which is needed for the pulse wave to propagate between two different portions of the artery. The PWP information obtaining means 70 includes a time difference calculating means for calculating, as a pulse-wave propagation time $DT_{RP}$, a time difference between a predetermined paint (e.g., R-wave) of the ECG waveform of each of periodic pulses successively detected by the ECG waveform detecting device 34 and a predetermined point (e.g., rising point, that is, minimum point) of the waveform of a corresponding one of periodic pulses of the photoelectric (volume) pulse wave detected by the probe 38, as shown in FIG. 3. The PWP information obtaining means 70 calculates a velocity $V_M$ (m/sec) of the pulse wave propagating through the artery of the subject, based on the calculated time $DT_{RP}$, according to the following expression (1) pre-stored in the ROM 31:

$$V_M = L/(DT_{RP} - T_{PEP}) \tag{1}$$

where L (m) is a length of the artery as measured from the left ventricle via the aorta to the position at which the probe 38 is set; and $T_{PEP}$ (sec) is a pre-ejection period between the R-wave of the ECG waveform of each pulse and the minimum point of the waveform of a corresponding pulse of an aortic pulse wave. The values L and $T_{PEP}$ are constants, respectively, and are experimentally obtained in advance.

Figure 4:
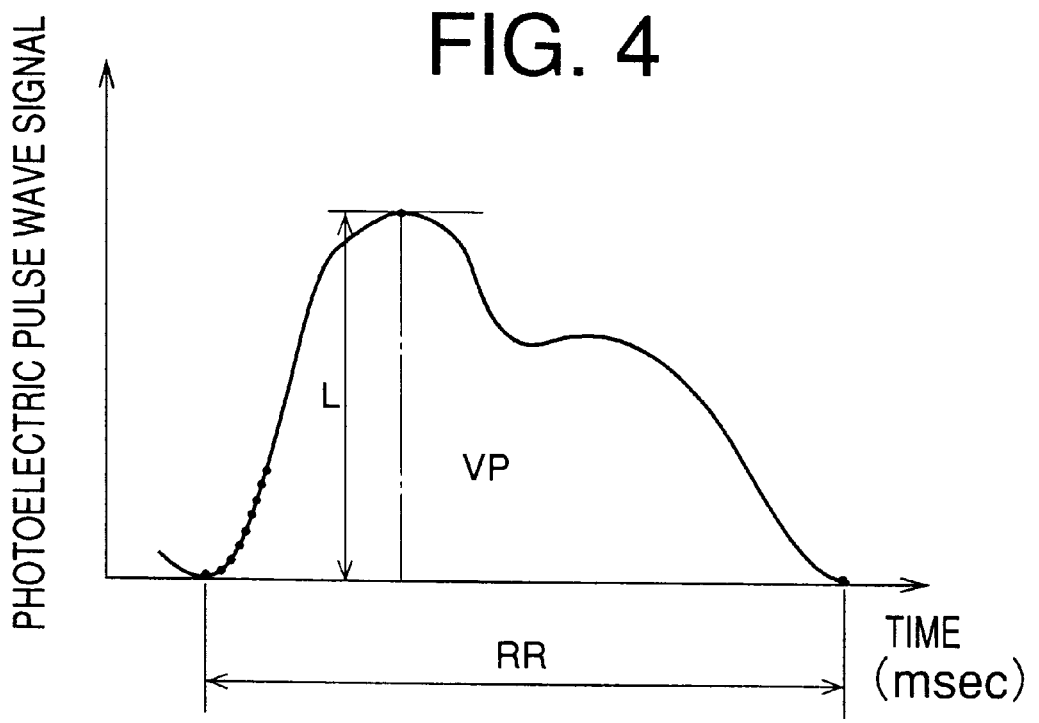
FIG. 4 is a view for explaining a volume-pulse-wave area VP.

A circulation information obtaining means 72 includes at least one of a heart rate (HR) information obtaining means 74 and a volume-pulse-wave area (VPWA) information obtaining means 76. The HR information obtaining means 74 obtains information which relates to a heart rate of a subject, such as a heart rate HR, a heart-beat period RR, a pulse rate, a pulse period, or the like. The VPWA information obtaining means 76 obtains information which relates to an area defined by a volume pulse wave from a peripheral portion of the subject. Specifically, as shown in FIG. 4, an area VP is defined by the waveform of each heartbeat-synchronous pulse of the photoelectric (volume) pulse wave detected by the probe 38, and is normalized based on a heart-beat period RR and an amplitude L of the pulse. The waveform of each pulse of the photoelectric pulse wave is defined by a series of data points indicative of respective magnitudes which are input at a predetermined interval such as several milliseconds to several tens of milliseconds. The area VP is obtained by integrating, in a heart-beat period RR, the respective magnitudes of the pulse of the photoelectric pulse wave being input at the predetermined interval, and then a normalized pulse-wave area NVP is obtained by calculating the following expression: NVP=VP/(RR×L). The volume-pulse-wave area information includes the area VP, a ratio VR of the area VP to the heart-beat period RR of the subject, a ratio VR' of a product of the area VP and the amplitude L of the photoelectric pulse wave to the heart-beat period RR, and a ratio of the area VP to a product of the heart-beat period RR and the amplitude L, that is, the normalized pulse-wave area NVP. Both of the heart rate information and the volume-pulse-wave area information change in relation with the intraarterial blood pressure of the subject. That is, the change of the blood pressure occurs due to the change of cardiac output on the proximal side of the subject and the change of peripheral vascular resistance on the distal side of the subject. The heart rate information reflects the amount of the cardiac output while the volume-pulse-wave area information reflects the magnitude of the peripheral vascular resistance.

A BP estimating means 80 calculates, according to a predetermined relationship between blood pressure, and pulse-wave propagation information and at least one of heart rate information and volume-pulse-wave area information, an estimated blood pressure of the subject, based on the obtained pulse-wave propagation information, and at least one of the obtained heart-rate information and the obtained volume-pulse-wave area information. For example, the blood pressure estimating means 80 calculates an estimated blood pressure EBP of the subject, based on a time $DT_{RP}$ obtained by the PWP information obtaining means 70, a period RR obtained by the HR information obtaining means 74, and a ratio VR obtained by the VPWA information obtaining means 76, according to the following expression (2) pre-stored in the ROM 31:

$$EBP = \alpha(1/DT_{RP}) + \beta RR + \gamma VR + \delta \quad (2)$$

where $\alpha$, $\beta$, $\gamma$ are predetermined coefficients and $\delta$ is a predetermined constant. The expression (2) shows a relationship between blood pressure of the subject, and time $DT_{RP}$, period RR, and ratio VR of the subject.

A coefficient determining means 82 selects, from a plurality of groups of predetermined coefficients ($\alpha$, $\beta$, $\gamma$) which respectively correspond to a plurality of blood-pressure ranges, one group of predetermined coefficients which corresponds to a reference value of the blood pressure of the subject, so that an estimated blood pressure EBP of the subject is calculated according to the expression (2) including the selected group of predetermined coefficients. The plurality of groups of pre determined coefficients are pre-stored in the ROM 31. For example, in the case where a systolic blood pressure value $BP_{SYS}$ measured using the cuff 10 by a BP measuring means 96 (which will be described below) is employed as a reference value of the blood pressure of the subject, the coefficients determining means 82 selects, from the pre-stored plurality of groups of predetermined coefficient which respectively correspond to the plurality of blood-pressure ranges, one group of predetermined coefficients which corresponds to the measured systolic blood pressure value $BP_{SYS}$. In this case, the BP estimating means 80 successively calculates an estimated systolic blood pressure value $EBP_{SYS}$. Further, each of the estimated blood pressure values EBP successively calculated by the BP estimating means 80 is employed as a reference value of the blood pressure, and the coefficient determining means 82 selects, from the pre-stored plurality of groups of predetermined coefficients which respectively correspond to the plurality of blood-pressure ranges, one group of predetermined coefficients which corresponds to the each estimated blood pressure value EBP. In place of the systolic blood pressure value $BP_{SYS}$, a diastolic blood pressure value $BP_{DIA}$ or a mean blood pressure value $BP_{MEAN}$ may be employed as the reference value of the blood pressure. When one group of predetermined coefficients which corresponds to the reference diastolic blood pressure value $BP_{DIA}$ is selected, the BP estimating means 80 calculates an estimated diastolic blood pressure $EBP_{DIA}$. When one group of predetermined coefficients which corresponds to the reference mean blood pressure $BP_{MEAN}$ is selected, the BP estimating means 80 calculates an estimated mean blood pressure value $EBP_{MEAN}$.

A constant determining means 83 determines the constant $\delta$ of the expression (2) used by the BP estimating means 80, by subtracting, from an actual blood pressure value of the subject which has been measured using the cuff 10 and has been used by the coefficient determining means 82 to select one group of predetermined coefficients $\alpha$, $\beta$, $\gamma$, the sum of the first product of the coefficient $\alpha$ and the inverse of a time $DT_{RP}$, and at least one of the second product of the coefficient $\beta$ and period RR, and the third product of the coefficient $\gamma$ and a ratio VR. The time $DT_{RP}$, the period RR, and the ratio VR are ones which have been obtained when the actual blood pressure value is measured using the cuff 10.

FIG. 5 illustrates one example of a plurality of groups of predetermined coefficients which respectively correspond to a plurality of blood-pressure ranges. In the figure, six groups of predetermined coefficients ($\alpha$, $\beta$, $\gamma$) correspond to six blood pressure ranges each defined by 40 mmHg. Usually, if the blood pressure of the subject increases, the inverse $(1/DT_{RP})$ of time difference $DT_{RP}$ tends to increase, and the period RR and the ratio VR tend to decrease. Accordingly, in FIG. 5, the coefficient $\alpha$ is a positive value, and the coefficients $\beta$ and $\gamma$ are negative values. The plurality of groups of predetermined coefficients are pre-stored in the ROM 31. Each of the plurality of groups of coefficients ($\alpha$, $\beta$, $\gamma$) are determined by applying a multiple regression analysis to many sets of information obtained from many living persons. Each of the sets of information includes a blood pressure value measured using a cuff, or the like, from a corresponding one of the persons, and a time $DT_{RP}$, a period RR, and a ratio VR obtained from the same person when the blood pressure is measured from the person. For example, best unbiased estimate values of $\alpha$, $\beta$, $\gamma$, $\delta$ of the expression (2) for each blood-pressure range are obtained by applying a least square method to at least four sets of information each of which includes three explanatory variables (independent variables), i.e., a time $DT_{RP}$, a period RR, and a ratio VR, and one objective variable (dependent variable), i.e., an estimated blood pressure EBP corresponding to the each blood-pressure range. The thus obtained unbiased estimate values of $\alpha$, $\beta$, $\gamma$ are stored in the ROM 31.

An autonomic nerve system (ANS) activity determining means 84 determines an activity of an autonomic nerve system of the subject, based on at least one of a blood-pressure relating information which changes in relation with a blood pressure of the subject and the heart rate information. The blood-pressure relating information may be a time $DT_{RP}$, a velocity $V_M$, an estimated blood pressure value EBP, or the like. More specifically, the ANS activity determining means 84 includes at least one of a sympathetic nerve system (SNS) activity determining means 86 and a parasympathetic nerve system (PNS) activity determining means 88. The SNS activity determining means 86 determines an activity of a sympathetic nerve system of the subject, based on a low-frequency component which is present in the fluctuations of the blood-pressure relating information and whose frequency is sufficiently or significantly lower than a respiration frequency of the subject. The PNS activity determining means 88 determines an activity of a parasympathetic nerve system of the subject, based on a high-frequency component which is present in the fluctuations of the heart rate information and whose frequency is around the respiration frequency of the subject.

A coefficient changing means 90 changes, based on the activity of the autonomic nerve system determined by the ANS determining means 84, at least one coefficient of the expression (2) used by the BP estimating means 80, so that the expression (2) including the changed coefficient amplifies a change of an estimated blood pressure of the subject from a prior estimated blood pressure of the subject. More specifically, the coefficient changing means 90 includes a judging means for judging whether or not the determined activity of the sympathetic nerve system is greater than an upper limit of a first reference range, whether or not the determined activity of the parasympathetic nerve system is smaller than a lower limit of a second reference range, whether or not the determined activity of the sympathetic nerve system is smaller than a lower limit of the first reference range, and whether or not the determined activity of the parasympathetic nerve system is greater than an upper limit of the second reference range.

The coefficient changing means 90 changes at least one of the coefficients ($\alpha$, $\beta$, $\gamma$) of the expression (2), to a greater coefficient, when the judging means makes at least one of a first positive judgment that the determined activity of the sympathetic nerve system is greater than the upper limit of the first reference range and a second positive judgement that the determined activity of the parasympathetic nerve system is smaller than the lower limit of the second reference range. Consequently, the expression (2) including the changed coefficient amplifies a change of an estimated blood pressure EBP of the subject, from the prior estimated blood pressure of the subject.

On the other hand, the coefficient changing means 90 changes at least one of the coefficients ($\alpha$, $\beta$, $\gamma$) of the expression (2), to a smaller coefficient, when the judging means makes at least one of a third positive judgment that the determined activity of the sympathetic nerve system is smaller than the lower limit of the first reference range and a fourth positive judgment that the determined activity of the parasympathetic nerve system is greater than the upper limit of the second reference range. Consequently, the expression (2) including the changed coefficient amplifies a change of an estimated blood pressure EBP of the subject from the prior estimated blood pressure of the subject.

Thus, at least one of the coefficients ($\alpha$, $\beta$, $\gamma$) of the expression (2) is changed to amplify a change of an estimated blood pressure of the subject, whereby an abnormality of the blood pressure is accurately and speedily recognized. The coefficient changing means 90 does not change any of the coefficients ($\alpha$, $\beta$, $\gamma$) of the expression (2) to a greater coefficient when the judging means makes a first negative judgment that the determined activity of the sympathetic nerve system is not greater than the upper limit of the first reference range and a second negative judgment that the determined activity of the parasympathetic nerve system is not smaller than the lower limit of the second reference range, and does not change any of the coefficients ($\alpha$, $\beta$, $\gamma$) of the expression (2) to a smaller coefficient when the judging means makes a third negative judgment that the determined activity of the sympathetic nerve system is not smaller than the lower limit of the first reference range and a fourth negative judgment that the determined activity of the parasympathetic nerve system is not greater than the upper limit of the second reference range.

There will be described the reason why one or more coefficients of the expression (2) are changed by the coefficient changing means 90. As described above, the heart rate information and the volume-pulse-wave area information respectively reflect the cardiac output and the peripheral vascular resistance, each of which causes a change of the intraarterial blood pressure of the subject. The cardiac output and the peripheral vascular resistance are adjusted by the sthenia and depression (i.e., activities) of the sympathetic nerve system and the parasympathetic nerve system. When at least one of the first positive judgment that the determined activity of the sympathetic nerve system is greater than the upper limit of the first reference range and the second positive judgment that the determined activity of the parasympathetic nerve system is smaller than the lower limit of the second reference range is made, it is estimated that the blood pressure will be increased. Therefore, at least one of the coefficients of the expression (2) used by the BP estimating means 80 is changed to a greater coefficient. When at least one of the third positive judgment that the determined activity of the sympathetic nerve system is smaller than the lower limit of the first reference range and the fourth positive judgment that the determined activity of the parasympathetic nerve system is greater than the upper limit of the second reference range is made, it is estimated that the blood pressure will be decreased. Therefore, at least one of the coefficients of the expression (2) is changed to a smaller coefficient.

Figure 8:
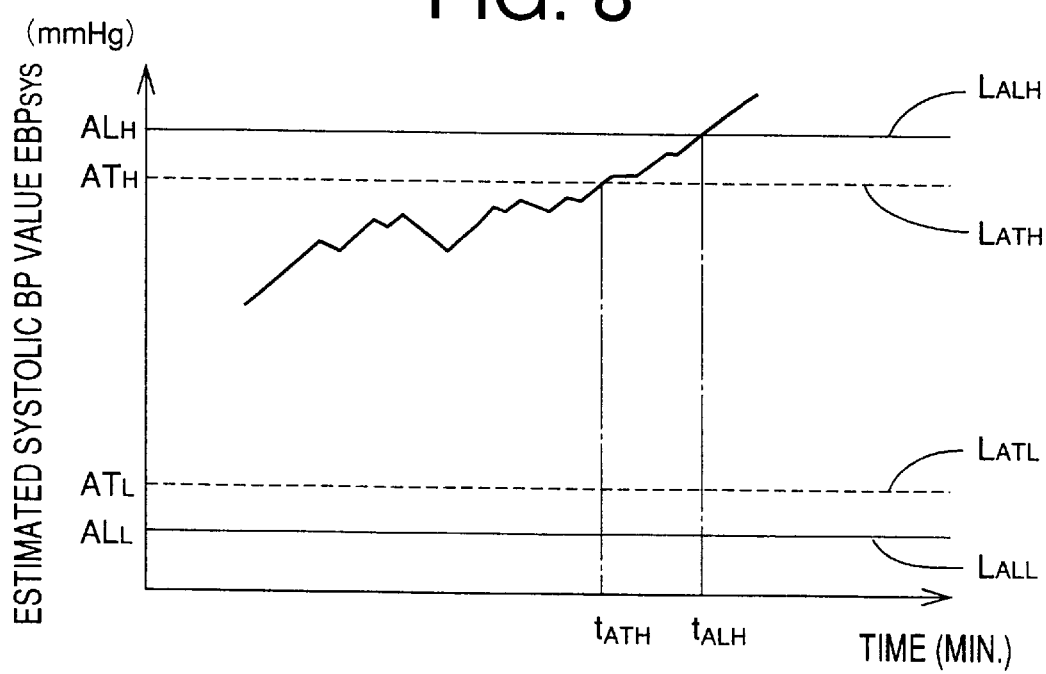
FIG. 8 is a view for illustrating a trend graph of estimated blood pressure EBP which is displayed by a display means 98.

A first judging means 92 judges whether or not a physical parameter which is obtained from the subject and which changes in relation with the blood pressure of the subject falls within a first reference range ($AL_L$–$AL_H$, FIG. 8). The first judging means 92 functions as an alarm judging means. The physical parameter is selected from the blood-pressure relating information which changes in relation with the blood pressure of the subject, the heart rate information which relates to the heart rate which changes to adjust the blood pressure on the proximal side of the subject, or the volume-pulse-wave area information which reflects the peripheral vascular resistance which changes to adjust the blood pressure on the distal side of the subject. The first reference range ($AL_L$–$AL_H$) is defined by a critical range in which the blood pressure of the subject indicates a need for an emergency medical treatment. The first reference range ($AL_L$–$AL_H$) may be a constant range of the parameter, or a predetermined range of the amount or rate of change of a current value of the parameter from a prior value of the same obtained when the last blood pressure value is measured using the cuff 10.

A second judging means 94 judges whether or not the physical parameter falls within a second reference range ($AT_L$–$AT_H$) which is contained in the first reference range ($AL_L$–$AL_H$). The second judging means 94 functions as an alert judging means. For example, an upper limit $AT_H$ of the second reference range is determined at a value lower, by a predetermined value or percentage, than the upper limit $AL_H$ of the first reference range. A lower limit $AT_L$ of the second reference range is determined at a value higher, by a predetermined value or percentage, than the lower limit $AL_L$ of the first reference range.

A BP measuring means 96 automatically measures a blood pressure of the subject, based on variation of respective amplitudes of heartbeat-synchronous pulses of the pulse wave produced by changing a pressing pressure of the cuff 10, when the second judging means 94 makes a negative judgment that the physical parameter does not fall within the second reference range. For example, the BP measuring means 96 measures a systolic, a mean and a diastolic blood pressure value $BP_{SYS}$, $BP_{MEAN}$, $BP_{DIA}$, of the subject, according to a well-known oscillometric method, based on variation of respective amplitudes of pulses of the pulse wave represented by the pulse-wave signal $SM_1$ obtained while the pressing pressure of the cuff 10 which is quickly increased to a target value $P_{CM}$ (e.g., 180 mmHg), is slowly decreased at the rate of about 3 mmHg/sec.

A display means 98 displays, in a two-dimensional coordinate system defined by a first axis indicative of time and a second axis indicative of physical parameter or rate of change of the physical parameter, successively obtained data indicative of the physical parameter or the rate of change thereof along the first axis. Moreover, the display means 98 displays two first lines $L_{ALH}$, $L_{ALL}$ (indicated in solid lines in FIG. 8) which are indicative of the upper and lower limits of the first reference range, respectively, and which are parallel to the first axis, and two second lines $L_{ATH}$, $L_{ATL}$ (indicated in broken lines in FIG. 8) which are indicative of the upper and lower limits of the second reference range, respectively, and which are parallel to the first axis. Further, the display means 98 outputs a visible message indicating that the physical parameter does not fall within the first or second reference range or an audible message indicating that the physical parameter does not fall within the first or second reference range.

Next, there will be described the operation of the control device 28 of the BP estimating apparatus 8 by reference to the flow charts of FIGS. 6, 7 and 9.

Figure 6:
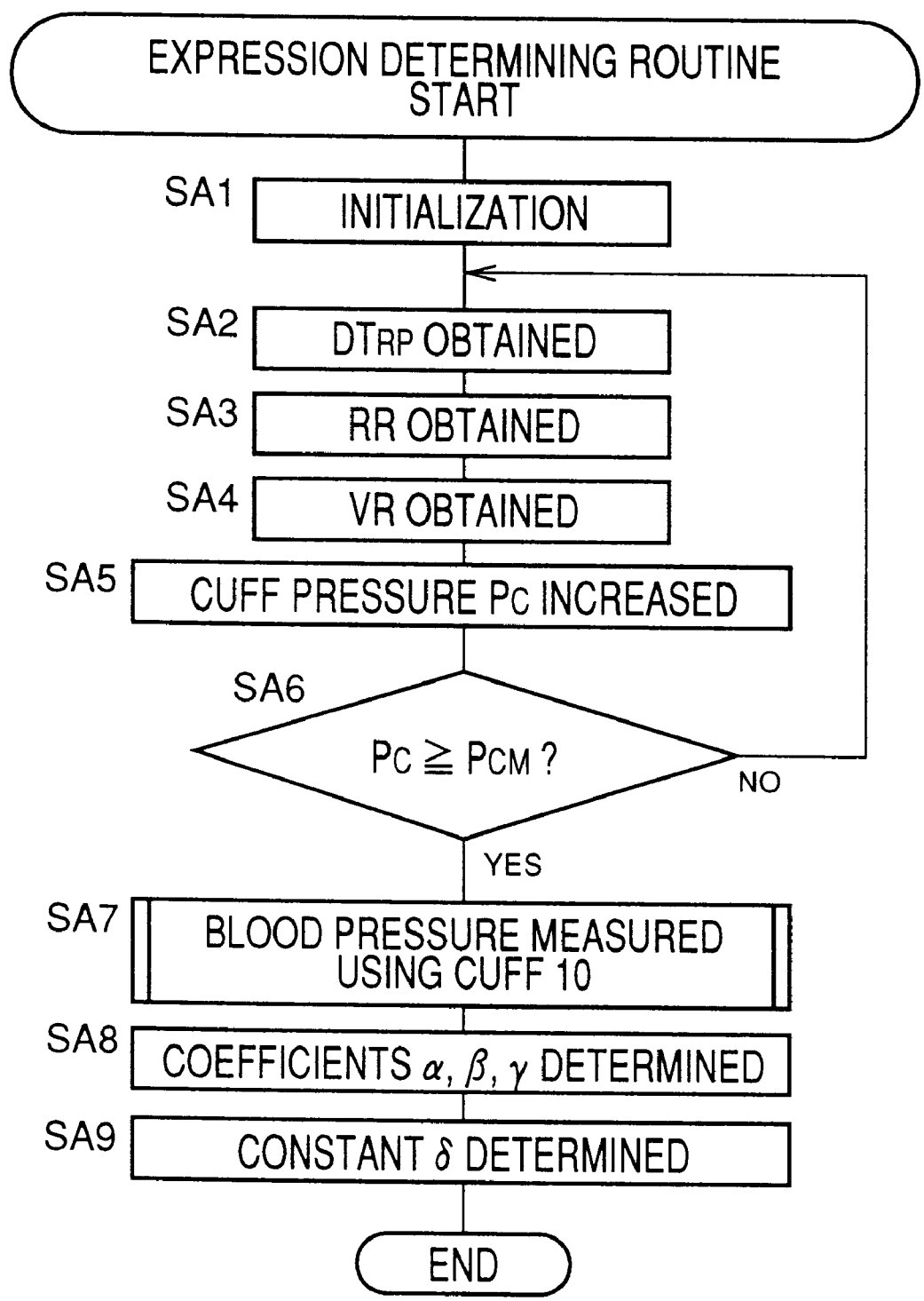
FIG. 6 is a flow chart representing an expression determining routine according to which the apparatus of FIG. 1 is operated.

The control of the CPU 29 begins with Step SA1 of the expression determining routine of FIG. 6, where flags, counters and registers (not shown) are reset. Step SA1 is followed by Step SA2. At Step SA2, the CPU 29 judges whether or not a R-wave of the ECG waveform of one pulse and a waveform of a corresponding pulse of the photoelectric pulse wave have been read in and, if a positive judgment is made, the CPU 29 calculates, as a pulse-wave propagation time $DT_{RP}$, a time difference between the R-wave of the ECG waveform of the pulse and the minimum point of the waveform of the corresponding pulse of the photoelectric pulse wave. Step SA2 corresponds to the PWP information obtaining means 70.

Step SA2 is followed by Step SA3 to measure, as a heart-beat period RR (sec), a time difference between the R-wave of the ECG waveform of the pulse read in Step SA2 of the current cycle and the R-wave of the ECG of the pulse read in the prior cycle. Step SA3 corresponds to the HR information obtaining means 74. Step SA3 is followed by Step SA4 to obtain a ratio VR (=VP/RR) of an area VP defined by the pulse of the photoelectric pulse wave read in at Step SA2, to the heart-beat period RR measured at Step SA3. Step SA4 corresponds to the VPWA information obtaining means 76. Steps SA3 and SA4 correspond to the circulation information obtaining means 72.

Next, the CPU 29 carries out Steps SA5, SA6, and SA7 corresponding to the BP measuring means 96. At Step SA5, the CPU 29 controls the selector valve 16 to its inflation position and controls the air pump 18 to start, thereby quickly increasing the cuff pressure $P_C$. At Step SA6, the CPU 29 judges whether the cuff pressure $P_C$ is equal to, or higher than, a predetermined target value $P_{CM}$ (e.g., 180 mmHg). If a negative judgement is made at Step SA6, Steps SA2 to SA5 and SA6 are repeated to increase the cuff pressure $P_C$ until a positive judgement is made.

Meanwhile, if a positive judgement is made at Step SA6, the control of the CPU 29 goes to Step SA7 to stop the air pump 18 and switch the selector valve 16 to its slow-deflation position, so as to slowly decrease the cuff pressure $P_C$ at a predetermined rate of about 3 mmHg/sec. The CPU 29 determines a systolic blood pressure value $BP_{SYS}$, a mean blood pressure value $BP_{MEAN}$ and a diastolic blood pressure value $BP_{DIA}$, according to a well known oscillometric blood pressure determining algorithm, based on the variation of respective amplitudes of pulses of the pulse wave represented by the pulse wave signal $SM_1$ obtained while the cuff pressure $P_C$ is slowly decreased. Step SA7 corresponds to the BP measuring means 96. At Step SA7, the CPU 29 additionally determines a pulse rate of the subject based on the interval between two successive pulses of the pulse wave signal $SM_1$. The CPU 29 controls the display 32 to display the thus determined blood pressure values and the pulse rate value. Then, the CPU 29 switches the selector valve 16 to its quick-deflation position.

Next, Step SA7 is followed by Step SA8 to select, from a plurality of groups of predetermined coefficients ($\alpha$, $\beta$, $\gamma$) which correspond to a plurality of blood-pressure ranges, respectively, one group of predetermined coefficients which corresponds to the systolic blood pressure value $BP_{SYS}$ measured at Step SA7, so that an estimated blood pressure EBP is calculated according to the expression (2) including the selected group of predetermined coefficients. Step SA8 corresponds to the coefficient determining means 82.

Subsequently, the CPU 29 carries out Step SA9 corresponding to the constant determining means 83. At Step SA9, the CPU 29 determines the constant 6 of the expression (2), by subtracting, from the systolic blood pressure value $BP_{SYS}$ which has been determined at Step SA7 and has been used at Step SA8 to select one group of predetermined coefficients $\alpha$, $\beta$, $\gamma$, the sum of the first product of the coefficient $\alpha$ and the inverse of the time $DT_{RP}$ obtained at Step SA2, the second product of the coefficient $\beta$ and the period RR obtained at Step SA3, and the third product of the coefficient $\gamma$ and the ratio VR obtained at Step SA4. Assuming that the time $DT_{RP}$ period RR, and ratio VR obtained at Steps SA2, SA3, and SA4 are represented by symbols $DT_{RP0}$, period $RR_0$, and ratio $VR_0$, the constant $\delta$ is obtained according to the following expressions (3) and (4):

$$BP_{SYS} = \alpha(1/DT_{RP0}) + \beta RR_0 + \gamma VR_0 + \delta \quad (3)$$

$$\delta = BP_{SYS} - \{\alpha(1/DT_{RP0}) + \beta RR_0 + \gamma VR_0\} \quad (4)$$

Figure 7:
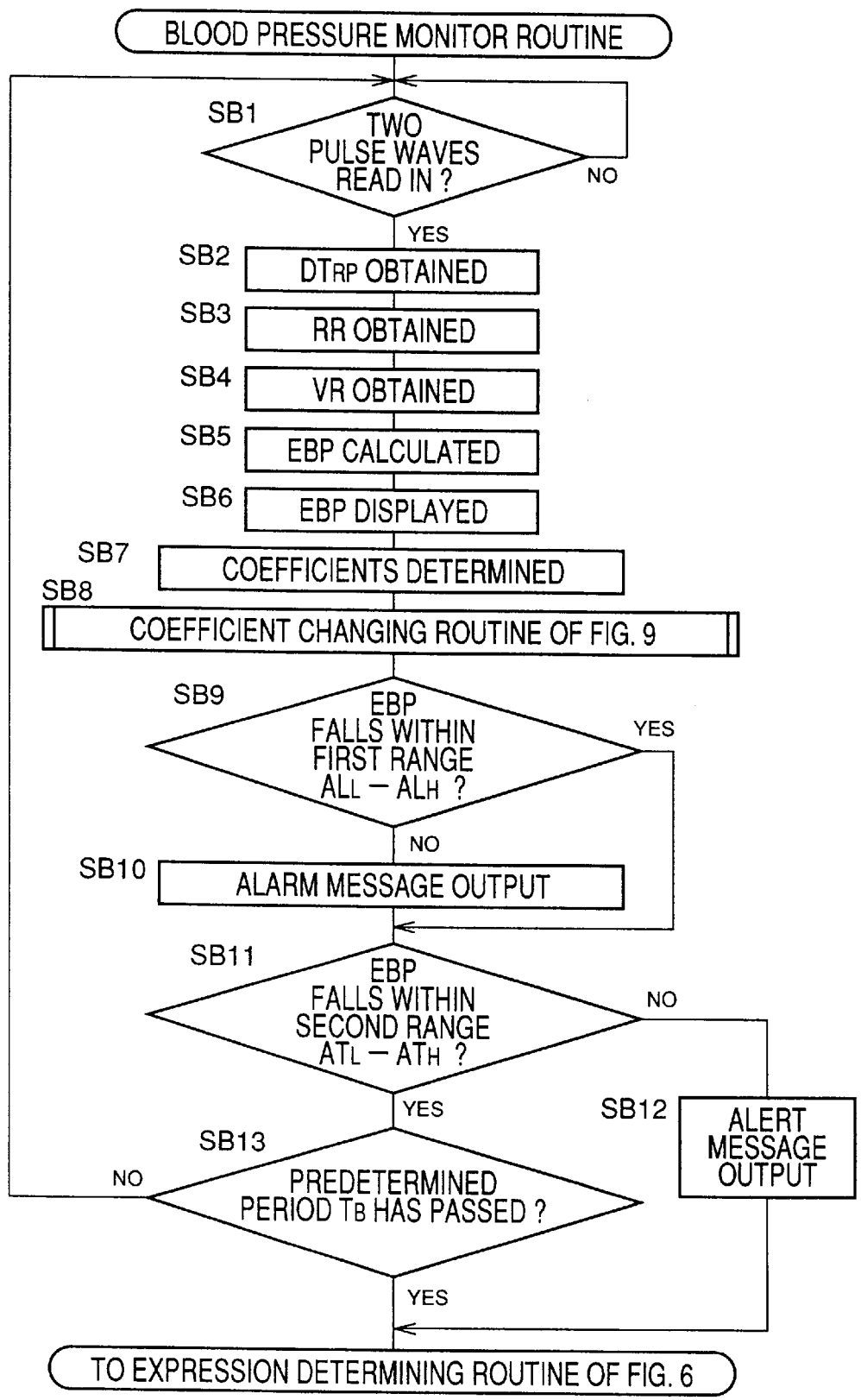
FIG. 7 is a flow chart representing a blood pressure monitor routine according to which the apparatus of FIG. 1 is operated.

Then, the control of the CPU 29 goes to Step SB1 of the blood pressure monitor routine of FIG. 7.

At Step SB1, the CPU 29 judges whether or not a R-wave of the ECG waveform of one pulse and a waveform of a corresponding pulse of the photoelectric pulse wave have been read in. If a negative judgment is made at Step SB1, the control of the CPU 29 waits until a positive judgment is made at Step SB1. If a positive judgment is made at Step SB1, the control of the CPU 29 goes to Steps SB2, SB3, and SB4 which are the same as Steps SA2, SA3, and SA4. Step SB2 corresponds to the PWP information obtaining means 70. Step SB3 corresponds to the HR information obtaining means 74. Step SB4 corresponds to the VPWA information obtaining means 76. Thus, the CPU 29 calculates a time $DT_{RP}$, a period RR, and a ratio VR at Steps SB2, SB3, and SB4, respectively.

Step SB4 is followed by Step SB5 corresponding to the BP estimating means 80. At Step SB5, the CPU 29 calculates an estimated systolic blood pressure value $EBP_{SYS}$, based on the time $DT_{RP}$, the heart-beat period RR, and the ratio VR obtained at Steps SB2 to SB4, according to the expression (2) including the group of predetermined coefficients α, β, γ selected at Step SA8 and the constant δ determined at Step SA9.

Step SB5 is followed by Step SB6 corresponding to the display means 98. At Step SB6, the CPU 29 operates the display 32 to display, in a two-dimensional coordinate system defined by a first axis indicative of time and a second axis indicative of blood pressure as shown in FIG. 8, estimated systolic blood pressure values $EBP_{SYS}$ successively calculated at Step SB5. The two-dimensional coordinate system is displayed in a predetermined part of the display 32. Moreover, the display 32 displays two first lines $L_{ALH}$, $L_{ALL}$ (indicated in solid lines in FIG. 8) which are indicative of the upper and lower limits of the first reference (alarm) range, respectively, and which are parallel to the first axis, and two second lines $L_{ATH}$, $L_{ATL}$ (indicated in broken lines in FIG. 8) which are indicative of the upper and lower limits of the second reference (alert) range contained in the first reference range, respectively, and which are parallel to the first axis.

Step SB6 is followed by Step SB7 corresponding to the coefficient determining means 82. At Step SB7, the CPU 29 employs, as a reference value of the blood pressure, the estimated blood pressure value $EBP_{SYS}$ calculated at Step SB5, and selects, from the pre-stored plurality of groups of predetermined coefficients, one group of predetermined coefficients. Since the coefficients of the expression (2) are determined based on each of the estimated blood pressure values $EBP_{SYS}$ successively calculated at Step SB5, the accuracy of blood pressure estimation is improved.

Figure 9:
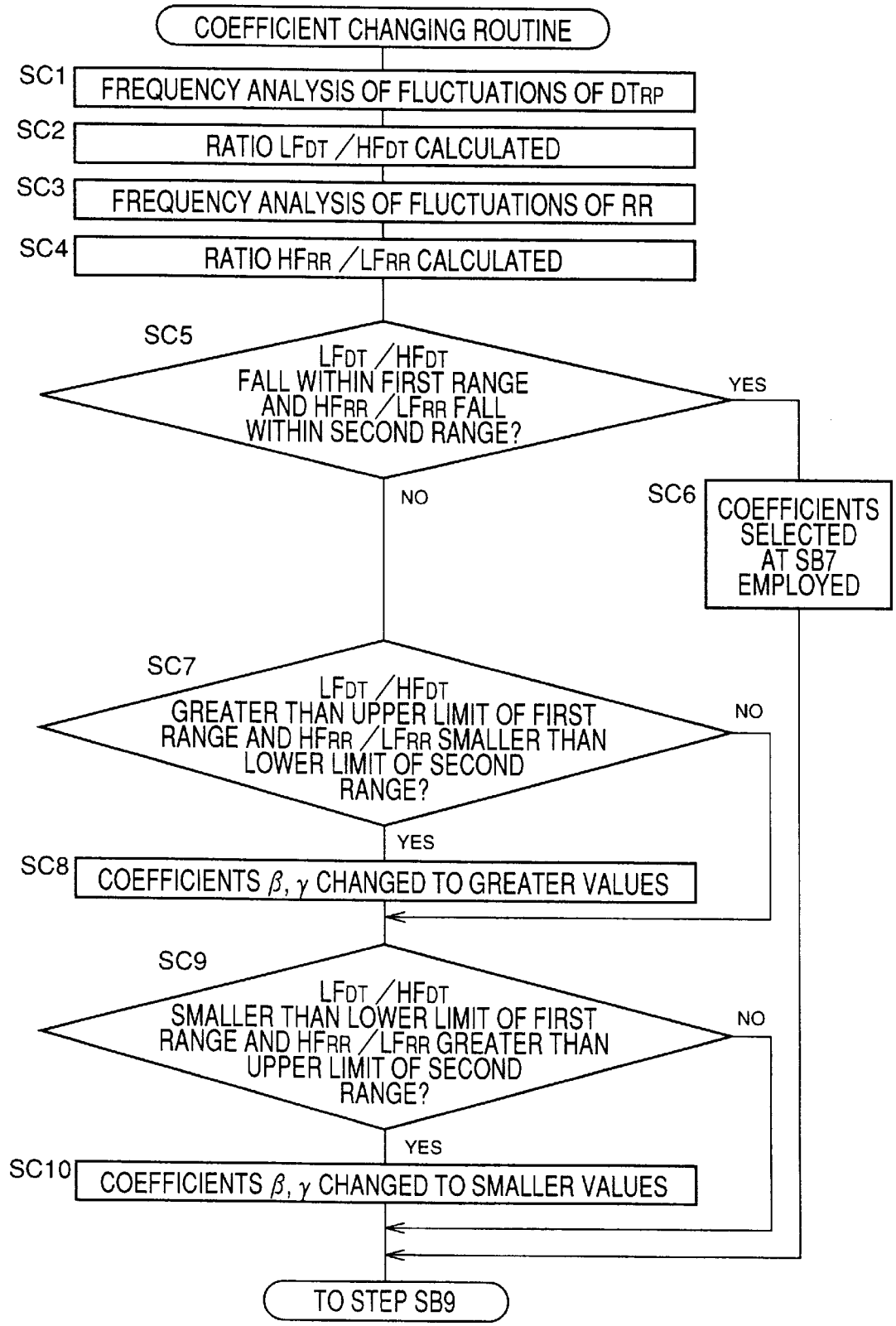
FIG. 9 is a flow chart representing a coefficient changing routine carried out at Step SB8 of FIG. 7.

Step SB7 is followed by Step SB8 to execute a coefficient changing routine shown in FIG. 9. In the routine shown in FIG. 9, the CPU 29 judges whether or not the coefficients of the expression (2) which are determined at Step SB7 should be changed, based on the time $DT_{RP}$ and the period RR which are obtained at Steps SB2 and SB3.

Figure 10:
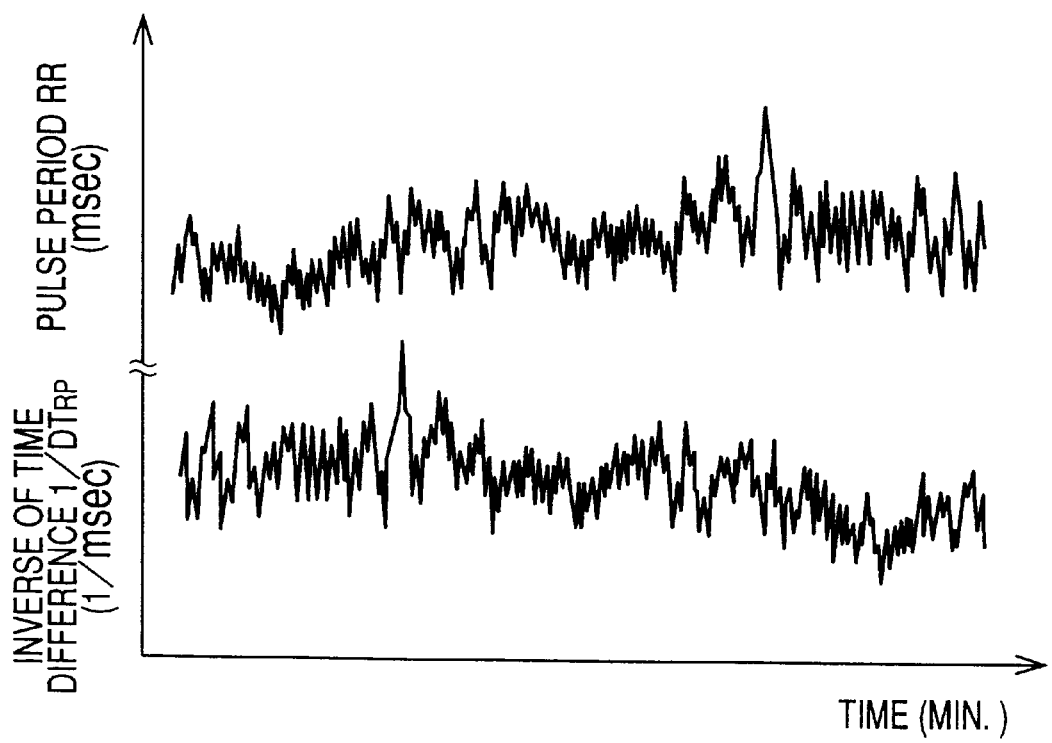
FIG. 10 is a view for illustrating fluctuations of heart-beat period RR and fluctuations of inverse of time difference $DT_{RP}$ which are obtained by the operation of the electric control device 28 of the apparatus of FIG. 1.
Figure 11:
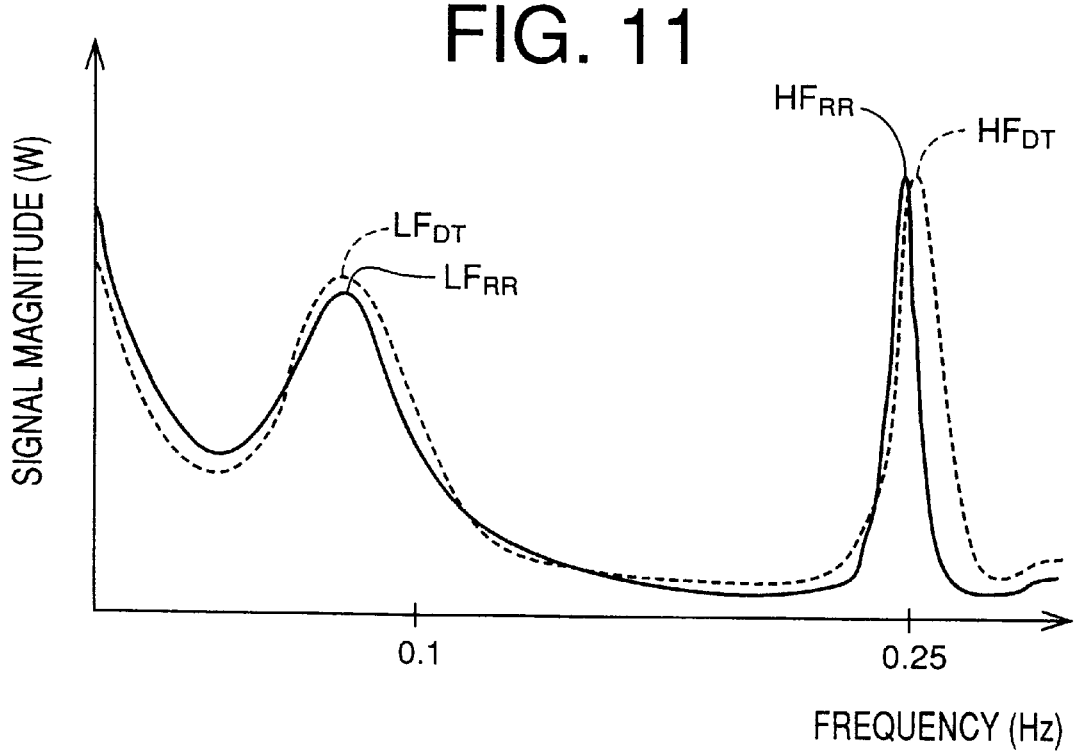
FIG. 11 is a view for illustrating spectrums which are obtained by applying a frequency analysis to the fluctuations of the period RR and the fluctuations of the inverse of the time difference $DT_{RP}$.

At Step SC1 of the flow chart of FIG. 9, the CPU 29 performs a frequency analysis of fluctuations of the time $DT_{RP}$ successively obtained at Step SB2. In FIG. 10, fluctuations of the inverse $(1/DT_{RP})$ of the time $DT_{RP}$ are indicated. By performing the frequency analysis (spectrum analysis) of the fluctuations of the inverse of the time $DT_{RP}$ with a fast Fourier transformation method or an autoregression method, a spectrum as shown in a broken line in FIG. 11 is obtained. The spectrum includes a high-frequency component $HF_{DT}$ having a frequency around a respiration frequency of the subject and a low-frequency component $LF_{DT}$ having a frequency around one third to one fourth of the respiration frequency of the subject.

Step SC1 is followed by Step SC2 to calculate, as an index indicative of an activity of the sympathetic nerve system, a ratio $(LF_{DT}/HF_{DT})$ of a magnitude or amplitude of the low-frequency component $LF_{DT}$ to a magnitude or amplitude of the high-frequency component $HF_{DT}$, which are obtained at Step SC1. It is generally known that the magnitude of the low-frequency signal component $LF_{DT}$ can be employed as a quantitative index indicative of the activity of the sympathetic nerve system. Since the magnitude of the high-frequency signal component $HF_{DT}$ is not influenced by the activity of the autonomic nerve system, the ratio $(LF_{DT}/HF_{DT})$ is employed as a quantitative index indicative of the activity of the sympathetic nerve system which is not influenced by the measurement conditions. Steps SC1 and SC2 correspond to the SNS activity determining means 86.

Step SC2 is followed by Step SC3. At Step SC3, the CPU 29 performs a frequency analysis of fluctuations of the heart-beat period RR successively obtained at Step SB3. In FIG. 10, fluctuations of the period RR are indicated. By performing the frequency analysis (spectrum analysis) of the fluctuations of the period RR with a fast Fourier transformation method or an autoregression method, a spectrum as shown in a solid line in FIG. 11 is obtained. This spectrum includes a high-frequency component $HF_{RR}$ having a frequency around the respiration frequency of the subject and a low-frequency component $LF_{RR}$ having a frequency around one third to one fourth of the respiration frequency of the subject, like the spectrum obtained by the frequency analysis of the inverse $(1/DT_{RP})$ of the time $DT_{RP}$.

Step SC3 is followed by Step SC4 to calculate, as an index indicative of an activity of the parasympathetic nerve system, a ratio $(HF_{RR}/LF_{RR})$ of a magnitude or amplitude of the high-frequency component $HF_{RR}$ to a magnitude or amplitude of the low-frequency component $LF_{RR}$. It is generally known that the magnitude of the high-frequency signal component $HF_{RR}$ can be employed as a quantitative index indicative of the activity of the parasympathetic nerve system. Since the magnitude of the low-frequency signal component $LF_{RR}$ is not influenced by the activity of the autonomic nerve system, the ratio $(HF_{RR}/LF_{RR})$ is employed as a quantitative index indicative of the activity of the parasympathetic nerve system which is not influenced by the measurement conditions. Steps SC3 and SC4 correspond to the PNS activity determining means 88. Steps SC1 to SC4 correspond to the ANS activity determining means 84.

Next, the control of the CPU 29 goes to Step SC5. At Step SC5, the CPU 29 judges whether or not the index $(LF_{DT}/HF_{DT})$ indicative of the activity of the sympathetic nerve system obtained at Step SC2 falls within a first reference range, and whether or not the index $(HF_{RR}/LF_{RR})$ indicative of the activity of the parasympathetic nerve system falls within a second reference range. The above first and second ranges are predetermined so as to judge the sthenia or depression (i.e., activity) of the sympathetic nerve system and the parasympathetic nerve system, respectively. Each of the first and the second reference ranges may be a constant range of the corresponding index $LF_{DT}/HF_{DT}$, $HF_{RR}/LF_{RR}$, or a predetermined range of the amount or rate of change of a current value of the corresponding index $LF_{DT}/HF_{DT}$, $HF_{RR}/LF_{RR}$, from a prior value thereof obtained when the last blood pressure value is measured using the cuff 10.

If a positive judgement is made at Step SC5, that is, the activity of the autonomic nerve system is relatively stable, the control of the CPU 29 goes to Step SC6. At Step SC6, the CPU 29 employs, as the coefficients of the expression (2), the group of predetermined coefficients which is selected at Step SB7. Thus, this routine of FIG. 9 is terminated and the control of the CPU 29 goes to Step SB9. Even in the case where the coefficients of the expression (2) have been changed at Step SC8 or SC10 in the cycle prior to the current cycle, the coefficients selected at Step SB7 in the current cycle are employed.

On the other hand, if a negative judgment is made at Step SC5, the control of the CPU 29 goes to Step SC7. At Step SC7, the CPU 29 judges whether or not the determined index $(LF_{DT}/HF_{DT})$ indicative of activity of the sympathetic nerve system is greater than an upper limit of the first reference range and simultaneously determined index $(HF_{RR}/LF_{RR})$ indicative of the parasympathetic nerve system is smaller than a lower limit of the second reference range. If a negative judgment is made at Step SC7, the control of the CPU 29 goes to Step SC9. If a positive judgment is made at Step SC7, the control of the CPU 29 goes to Step SC8. From the positive judgment at Step SC7, it is estimated that the cardiac output and the peripheral vascular resistance have largely changed to increase the blood pressure of the subject, due to the sthenia of the sympathetic nerve system and the depression of the parasympathetic nerve system. At Step SC8, the change of the estimated blood pressure EBP calculated by the expression (2) is amplified to more safely monitor the blood pressure of the subject. That is, the coefficients are changed to raise the estimated blood pressure EBP which is obtained according to the expression (2). Specifically, the CPU 29 changes the coefficients β, γ of the period RR and the ratio VR of the expression (2), to greater values, respectively, since the terms of the period RR and the ratio VR reflect the cardiac output and the peripheral vascular resistance, respectively. For example, the coefficients $β_0$, $γ_0$ ($β_0<0$, $γ_0<0$) determined at Step SB7 are respectively changed to half values $0.5β_0$, $0.5γ_0$.

Step SC8 is followed by Step SC9 to judge whether or not the determined index ($LF_{DT}/HF_{DT}$) indicative of the activity of the sympathetic nerve system is smaller than a lower limit of the first reference range and simultaneously the determined index ($HF_{RR}/LF_{RR}$) indicative of the activity of the parasympathetic nerve system is greater than an upper limit of the second reference range. If a negative judgment is made at Step SC9, this routine of FIG. 9 is terminated and the control of the CPU 29 goes to Step SB9. If a positive judgment is made at Step SC9, the control of the CPU 29 goes to Step SC10. From the positive judgment at Step SC9, it is estimated that the cardiac output and the peripheral vascular resistance have largely changed to decrease the blood pressure of the subject, due to the depression of the sympathetic nerve system and the sthenia of the parasympathetic nerve system. At Step SC10, the change of the estimated blood pressure EBP calculated according to the expression (2) is amplified to more safely monitor the blood pressure of the subject. That is, the coefficients are changed to reduce the estimated blood pressure EBP which is obtained according to the expression (2). Specifically, the CPU 29 changes the coefficients β, γ of the time RR and the ratio VR of the expression (2), to smaller values, respectively. For example, the coefficients $β_0$, $γ_0$ are respectively changed to twice values $2β_0$, $2γ_0$. Steps SC5–SC10 correspond to the coefficient changing means 90.

Referring back to FIG. 7, at Step SB9, the CPU 29 judges whether or not the estimated blood pressure EBP calculated at Step SB5 falls within a first reference range ($AL_L$–$AL_H$). For example, the CPU 29 judges whether or not the estimated blood pressure EBP is smaller than a lower limit $AL_L$ of the first reference range, and whether or not the estimated blood pressure EBP is greater than an upper limit $AL_H$ of the first reference range. The upper limit $AL_H$ of the first reference range is set at a value which is, by 30%, greater than an initial estimated blood pressure EBP calculated at Step SB5. The lower limit $AL_L$ of the first reference range is set at a value which is, by 30%, smaller than the initial estimated blood pressure EBP calculated at Step SB5. Step SB9 corresponds to the first judging means 92.

If a positive judgment is made at Step SB9, the control of the CPU 29 goes to Step SB11. On the other hand, if a negative judgment is made at Step SB9, the control of the CPU 29 goes to Step SB10. At Step SB10, the CPU 29 displays, on the display device 32, a visible message (e.g., characters or symbols) indicating that the estimated blood pressure EBP does not fall within the first reference range, and outputs, to the speaker of the display 32 (not shown), an audible message (e.g., alarm sounds or voice sounds) indicating that the estimated blood pressure EBP does not fall within the first reference range. Step SB10 corresponds to the display means 98.

Next, at Step SB11, the CPU 29 judges whether or not the estimated blood pressure EBP calculated at Step SB5 falls within a second reference range ($AT_L$–$AT_H$). For example, the CPU 29 judges whether or not the estimated blood pressure EBP is smaller than a lower limit $AT_L$ of the second reference range, and whether or not the estimated blood pressure EBP is greater than an upper limit $AT_H$ of the second reference range. The upper limit $AT_H$ is set at a value which is, by 15 mmHg, smaller than the upper limit $AL_H$ of the first reference range. The lower limit $AT_L$ is set at a value which is, by 15 mmHg, greater than the lower limit $AL_L$ of the first reference range. Step SB11 corresponds to the second judging means 94.

If a negative judgement is made at Step SB11, the control of the CPU 29 goes to Step SB12. At Step SB12, the CPU 29 displays, on the display device 32, a visible message (e.g., characters or symbols) indicating that the estimated blood pressure EBP does not fall within the second reference range, and outputs, to the speaker, an audible message (e.g., alarm sounds or voice sounds) indicating that the estimated blood pressure EBP does not fall within the second reference range. Step SB12 corresponds to the display means 98. Step SB12 is followed by the routine of FIG. 6 to execute the blood pressure measurement with the cuff 10. As shown in FIG. 8, in the present embodiment, the blood pressure measurement with the cuff 10 is executed at a time point $t_{ATH}$. Accordingly, the blood pressure measured using the cuff 10 can be obtained at the time point $t_{ATH}$ earlier than a time point $t_{ALH}$ (shown in FIG. 8) when the blood pressure measurement with the cuff 10 is started based on only the judgment that the estimated blood pressure EBP does not fall within the first reference range.

If a positive judgment is made at Step SB11, the control of the CPU 29 goes to Step SB13. At Step SB13, the CPU 29 judges whether or not a predetermined period $T_B$ has passed after the last blood pressure is measured using the cuff 10 at Step SA7. The predetermined period $T_B$ is a relatively long time period such as several minutes or several tens of minutes. If a negative judgment is made at Step SB13, the control of the CPU 29 returns to Step SB1. If a positive judgment is made at Step SB13, the control of the CPU goes to the routine of FIG. 6 to execute the blood pressure measurement using the cuff 10.

In the above described embodiment, the blood pressure estimating means 80 (Step SB5) calculates, according to the predetermined relationship (expression (2)) between estimated blood pressure EBP, and time $DT_{RP}$, period RR, and ratio VR, the estimated blood pressure value $EBP_{SYS}$ of the subject, based on the obtained time $DT_{RP}$, the obtained period RR, and the obtained ratio VR. Thus, the present apparatus 8 can obtain the estimated blood pressure $EBP_{SYS}$ with high accuracy. In the present embodiment, the estimated blood pressure is estimated based on, in addition to the time $DT_{RP}$, the period RR as the parameter on the side of the heart of the subject which changes in relation with the blood pressure of the subject and the ratio VR as the parameter on the side of a peripheral portion of the subject which changes in relation with the blood pressure of the subject. Thus, it is not needed to frequently calibrate the present apparatus 8 based on an actual blood pressure BP of the subject measured using the cuff 10, because the estimated blood pressure $EBP_{SYS}$ enjoys higher accuracy in comparison with the estimated blood pressure which is estimated based on only the time $DT_{RP}$ as the first information.

In the above embodiment, the coefficients α, β, γ, are determined by applying a multiple regression analysis to many sets of information obtained from many living persons. Each of the sets of information includes a blood pressure obtained from a corresponding one of the persons, and a time $DT_{RP}$, a period RR, and a ratio VR obtained from the same person when the blood pressure is obtained from the person. Thus, the present apparatus 8 can obtain a useful relationship for calculating an estimated blood pressure EBP.

While the present invention has been described in its preferred embodiment by reference to the drawings, it is to be understood that the invention may otherwise be embodied.

While in the illustrated embodiment the expression (2) used by the blood pressure estimating means 80 (Step SB5) for calculating the estimated blood pressure EBP employs both of the heart-beat period RR as the heart rate information and the volume-pulse-wave area ratio VR as the volume-pulse-wave area information, either one of the period RR and the ratio VR may be omitted.

In the illustrated embodiment, the expression (2) for calculating the estimated blood pressure EBP is a liner expression. However, the expression (2) may be a quadratic or higher-order expression. Moreover, the expression (2) may include a trigonal function or logarithm function. For example, the following expression (5) or (6) may be employed:

$$EBP=\alpha(1/DT_{RP})+\gamma VR^2+\delta \quad (5)$$

where α, γ are coefficients and δ is a constant.

$$EBP=\alpha(1/DT_{RP})+\beta\log(RR)+\gamma VR+\delta \quad (6)$$

where α, β, γ are coefficients and δ is a constant.

In the illustrated embodiment, every estimated blood pressure EBP is calculated according to only the single expression (2). However, an estimated blood pressure EBP may be calculated according one of a plurality of different expressions which corresponds to a reference blood pressure of the subject. The one expression is selected from the different expressions which respectively correspond to a plurality of blood-pressure ranges, in the same manner as the manner in which one group of coefficients is selected for the single expression (2).

In the illustrated embodiment, at Steps SA8 and SB7 corresponding to the coefficient determining means 82, the three coefficients α, β, γ are determined based on a reference blood pressure of the subject. However, only one or two of the three coefficients which influences or influence the estimated blood pressure EBP may be selected based on the reference blood pressure, and the others or other may be constant values or value, because the influence of each coefficient on the estimated blood pressure EBP may change for the different blood-pressure ranges.

In the illustrated embodiment, the time $DT_{RP}$ is calculated based on the time difference between the R-wave of the ECG waveform and the minimum point of the waveform of the photoelectric pulse wave. However, the time $DT_{RP}$ may be calculated based on a time difference between a Q-wave of the ECG waveform of each pulse and the minimum point of the waveform of a corresponding pulse of the photoelectric pulse wave.

In the illustrated embodiment, an estimated blood pressure EBP is determined based on the R-wave of the ECG waveform of each heartbeat-synchronous pulse and the waveform of a corresponding pulse of the photoelectric pulse wave. However, an estimated blood pressure EBP may be determined based on every second pulse, or so on, of the ECG waveform and every second pulse of the photoelectric pulse wave.

It is to be understood that the present invention may be embodied with other changes and modifications that may occur to those skilled in the art without departing from the scope of the invention.

What is claimed is:

1. An apparatus for successively estimating an intraarterial blood pressure of a living subject, based on information non-invasively obtained from a circulatory organ of the subject, comprising:

first means for non-invasively obtaining, from the circulatory organ of the subject, first information which relates to velocity of propagation of a pulse wave which propagates through an artery of the subject;

second means for non-invasively obtaining, from the circulatory organ of the subject, second information which relates to an area defined by a volume pulse wave from a peripheral portion of the subject; and third means for estimating, according to a predetermined relationship between (A) blood pressure, and (B1) first information and (B2) second information, the intraarterial blood pressure of the subject, based on the first information obtained by the first means and the second information obtained by the second means.

2. An apparatus according to claim 1, further comprising fourth means for obtaining third information which relates to heart rate of the subject, and wherein the third means comprises means for estimating, according to a predetermined relationship between (A) blood pressure, and (B1) first information, (B2) second information, and (B3) third information, the intraarterial blood pressure of the subject, based on the obtained first information, the obtained second information, and the obtained third information.

3. An apparatus according to claim 2, wherein the first means comprises means for obtaining, as the fist information, a time, DT, needed for the pulse wave to propagate between two different portions of the artery, wherein the fourth means comprises means for obtaining, as the third information, a heart-beat period, RR, of the subject, and the second means comprises means for obtaining, as the second information, a ratio, VR, of the area of the volume pulse wave to the heart-beat period RR, and wherein the third means comprises means for estimating, according to the predetermined relationship between (A) blood pressure, EBP, and (B1) time DT, (B2) ratio VR, and (B3) period RR, defined by a following expression: $EBP=\alpha(1/DT)+\beta RR+\gamma VR+\delta$, where α, β, and γ are predetermined coefficients and δ is a predetermined constant, the intraarterial blood pressure of the subject, based on the obtained time DT, the obtained period RR, and the obtained ratio VR.

4. An apparatus according to claim 3, further comprising a memory which stores data indicative of the coefficients α, β, γ which are predetermined by applying a multiple regression analysis to a plurality of sets of information obtained from at least one living person, each of said sets of information comprising a blood pressure obtained from the person, and a time DT, a period RR, and a ratio VR obtained from said person when the blood pressure is obtained from said person.

5. An apparatus according to claim 1, wherein the second means comprises means for obtaining the second information selected from the group consisting of the area defined by the volume pulse wave, a ratio of the area to a heart-beat period of the subject, a ratio of the area to a product of the heart-beat period and an amplitude of the volume pulse wave, and a ratio of a product of the area and the amplitude to the heart-beat period.

6. An apparatus according to claim 1, wherein the first means comprises:

a first pulse-wave sensor and a second pulse-wave sensor which non-invasively detect the pulse wave from two different portions of the artery of the subject, respectively; and means for determining, as the first information, a time needed for the pulse wave to propagate between the two different portions.

7. An apparatus according to claim 2, wherein the first means comprises: a first pulse-wave sensor and a second pulse-wave sensor which non-invasively detect the pulse wave from two different portions of the artery of the subject, respectively; and means for determining as the first information, a time needed for the pulse wave to propagate between the two different portions, and wherein the fourth means comprises means for determining, as the third information, a time difference between respective predetermined points of successive two heartbeat-synchronous pulses of the pulse wave detected by one of the first and second pulse-wave sensors.

8. An apparatus according to claim 6, wherein the second means comprises one of the first and second pulse-wave sensors, said one pulse-wave sensor detecting the volume pulse wave from the peripheral portion of the subject.

9. An apparatus according to claim 6, wherein the first and second pulse-wave sensors comprise an electrocardiograph and a photoelectric oximeter.

10. A method of successively estimating an intraarterial blood pressure of a living subject, based on information non-invasively obtained from a circulatory organ of the subject, comprising the steps of:

non-invasively obtaining, from the circulatory organ of the subject, first information which relates to velocity of propagation of a pulse wave which propagates through an artery of the subject, non-invasively obtaining, from the circulatory organ of the subject, second information which relates to an area defined by a volume pulse wave from a peripheral portion of the subject, and estimating, according to a predetermined relationship between (A) blood pressure, and (B1) first information and (B2) second information, the intraarterial blood pressure of the subject, based on the obtained first information and the obtained second information.

11. A method according to claim 10, further comprising a step of obtaining third information which relates to heart rate of the subject, and wherein the step of estimating the intraarterial blood pressure of the subject comprises estimating, according to a predetermined relationship between (A) blood pressure, and (B1) first information, (B2) second information, and (B3) third information, the intraarterial blood pressure of the subject, based on the obtained first information, the obtained second information, and the obtained third information.

12. A method according to claim 11, wherein the step of obtaining the first information comprises obtaining a time, DT, needed for the pulse wave to propagate between two different portions of the artery, wherein the step of obtaining the third information comprises obtaining, as the third information, a heart-beat period, RR, of the subject and the step of obtaining the second information comprises obtaining, as the second information, a ratio, VR, of the area of the volume pulse wave to the heart-beat period RR, and wherein the step of estimating the intraarterial blood pressure of the subject comprises estimating, according to the predetermined relationship between (A) blood pressure, EBP, and (B1) time DT, (B2) ratio VR, and (B3) period RR, defined by a following expression: $EBP = \alpha(1/DT) + \beta RR + \gamma VR + \delta$, where $\alpha$, $\beta$, and $\gamma$ are predetermined coefficients and $\delta$ is a predetermined constant, the intraarterial blood pressure of the subject, based on the obtained time DT, the obtained period RR, and the obtained ratio VR.

13. A method according to claim 12, further comprising a step of determining the coefficients $\alpha$, $\beta$, $\gamma$ by applying a multiple regression analysis to a plurality of sets of information obtained from at least one living person, each of said sets of information comprising a blood pressure obtained from the person, and a time DT, a period RR, and a ratio VR obtained from said person when the blood pressure is obtained from said person.

14. A method according to claim 10, wherein the step of obtaining the second information comprises obtaining the second information selected from the group consisting of the area defined by the volume pulse wave, a ratio of the area to a heart-beat period of the subject, a ratio of the area to a product of the heart-beat period and an amplitude of the volume pulse wave, and a ratio of a product of the area and the amplitude to the hear-beat period.

* * * * *